(12) United States Patent
Heuer et al.

(10) Patent No.: US 11,849,982 B2
(45) Date of Patent: Dec. 26, 2023

(54) EXTENSION DEVICE FOR A BONE ANCHOR

(71) Applicant: Silony Medical International AG, Frauenfeld (CH)

(72) Inventors: Frank Heuer, Filderstadt (DE); Marc Sanders, GC Bunde (NL)

(73) Assignee: Silony Medical International AG, Frauenfeld (CH)

( * ) Notice: Subject to any disclaimer, the term of this patent is extended or adjusted under 35 U.S.C. 154(b) by 1033 days.

(21) Appl. No.: 16/623,990

(22) PCT Filed: Jun. 15, 2018

(86) PCT No.: PCT/EP2018/065987
§ 371 (c)(1),
(2) Date: Dec. 18, 2019

(87) PCT Pub. No.: WO2019/001990
PCT Pub. Date: Jan. 3, 2019

(65) Prior Publication Data
US 2020/0197052 A1    Jun. 25, 2020

(30) Foreign Application Priority Data
Jun. 27, 2017 (DE) .................... 10 2017 114 273.8

(51) Int. Cl.
*A61B 17/70* (2006.01)

(52) U.S. Cl.
CPC ...... *A61B 17/7085* (2013.01); *A61B 17/7032* (2013.01)

(58) Field of Classification Search
CPC .............. A61B 17/708; A61B 17/7083; A61B 17/7085
See application file for complete search history.

(56) References Cited

U.S. PATENT DOCUMENTS

| 7,520,879 B2 * | 4/2009 | Justis ................. A61B 17/7002 606/86 A |
| 8,439,924 B1 * | 5/2013 | McBride .............. A61B 17/708 606/104 |

(Continued)

OTHER PUBLICATIONS

International Search Report and Non-Translated Written Opinion Form PCT/IS/210 and PCT/ISA/237, International Application No. PCT/EP2018/065987, pp. 1-11, International Filing Date Jun. 15, 2018, dated Sep. 27, 2018.

(Continued)

*Primary Examiner* — Lynnsy M Summitt
(74) *Attorney, Agent, or Firm* — George McGuire

(57) ABSTRACT

The invention relates to an extension device for a bone anchor, in particular for a bone screw, in particular for a pedicle screw, in particular in minimally invasive spinal surgery, the device having an axial longitudinal direction, a peripheral direction concentric therewith, and a radial direction, wherein the extension device extends in the axial longitudinal direction and engages, by means of a radial projection, an engageable region on the head of the bone anchor in the longitudinal direction and also in the radial direction and can be supported against the head of the bone anchor in the opposite direction so that the extension device can thereby be fixed to the head of the bone anchor so as to be detachable, yet also rigid in the longitudinal direction and non-rotatable.

26 Claims, 12 Drawing Sheets

(56) References Cited

U.S. PATENT DOCUMENTS

| | | | | |
|---|---|---|---|---|
| 8,603,094 | B2* | 12/2013 | Walker | A61B 17/7086 |
| | | | | 606/86 A |
| 9,220,539 | B2* | 12/2015 | McBride | A61B 17/7076 |
| 9,510,875 | B2* | 12/2016 | Reitblat | A61B 17/708 |
| 9,532,814 | B2* | 1/2017 | Harper | A61B 17/8875 |
| 11,622,795 | B2* | 4/2023 | Suh | A61B 17/7002 |
| | | | | 606/86 A |
| 2009/0228054 | A1* | 9/2009 | Hoffman | A61B 17/7086 |
| | | | | 606/86 A |
| 2010/0137875 | A1* | 6/2010 | Marino | A61B 17/7037 |
| | | | | 606/86 A |
| 2011/0263945 | A1* | 10/2011 | Peterson | A61B 17/7086 |
| | | | | 606/300 |
| 2015/0066089 | A1 | 3/2015 | Nelson et al. | |
| 2018/0132911 | A1* | 5/2018 | Wu | A61B 17/7086 |

OTHER PUBLICATIONS

German Examination Report, pp. 1-10.

* cited by examiner

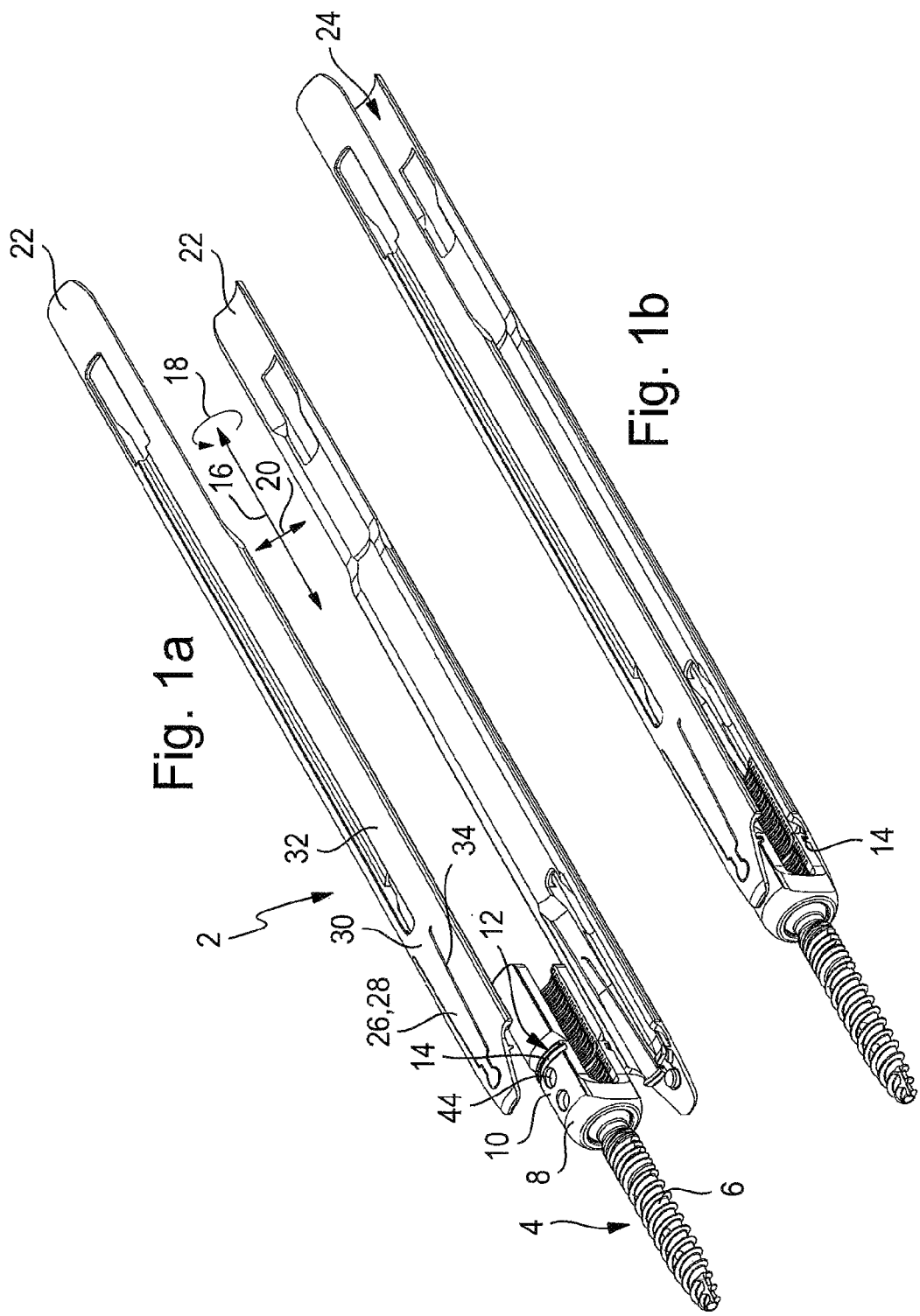

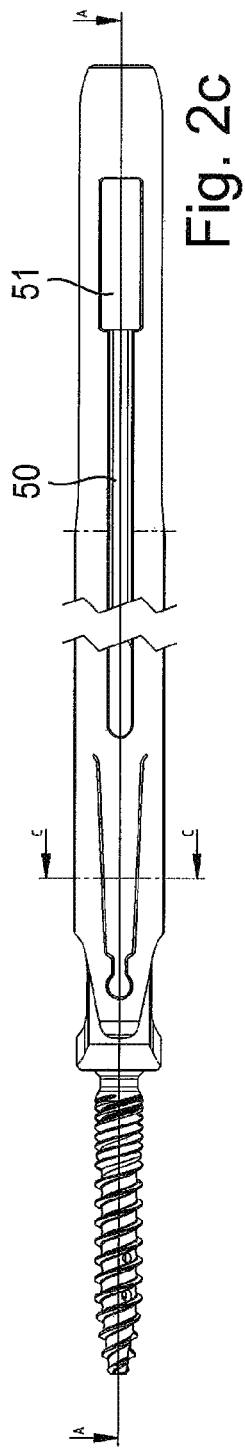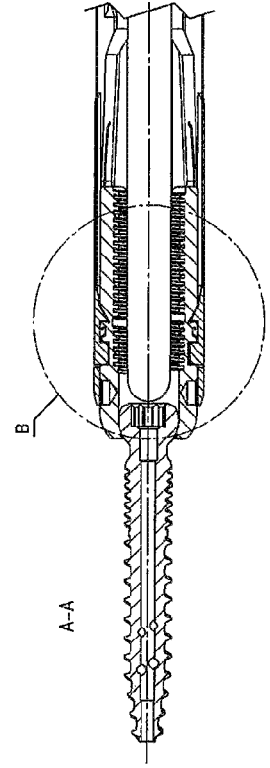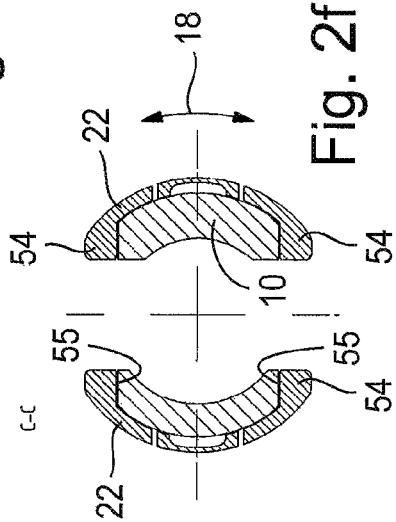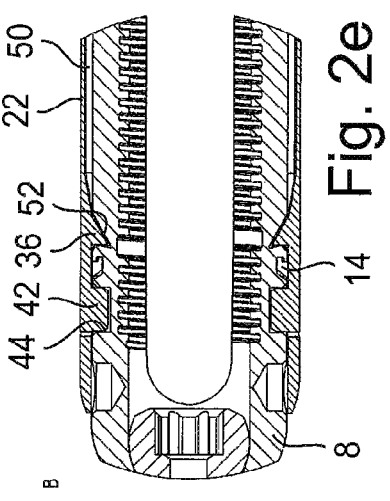

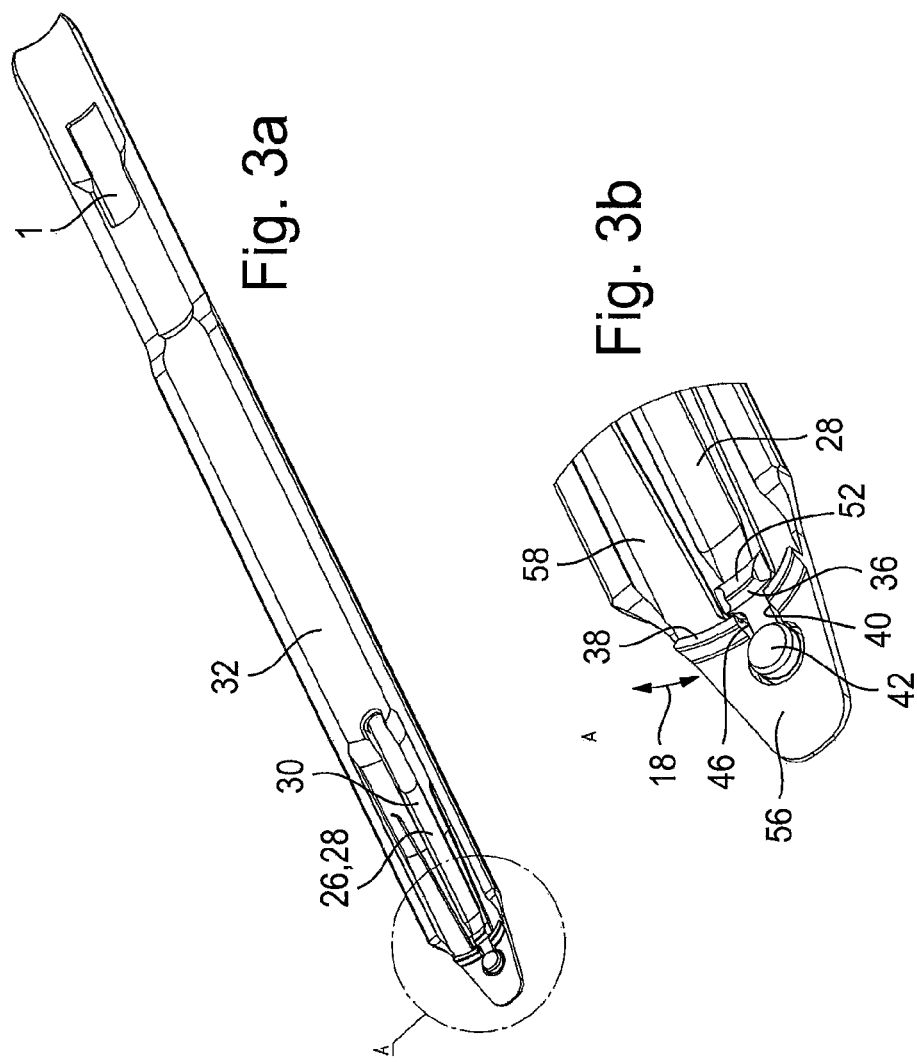

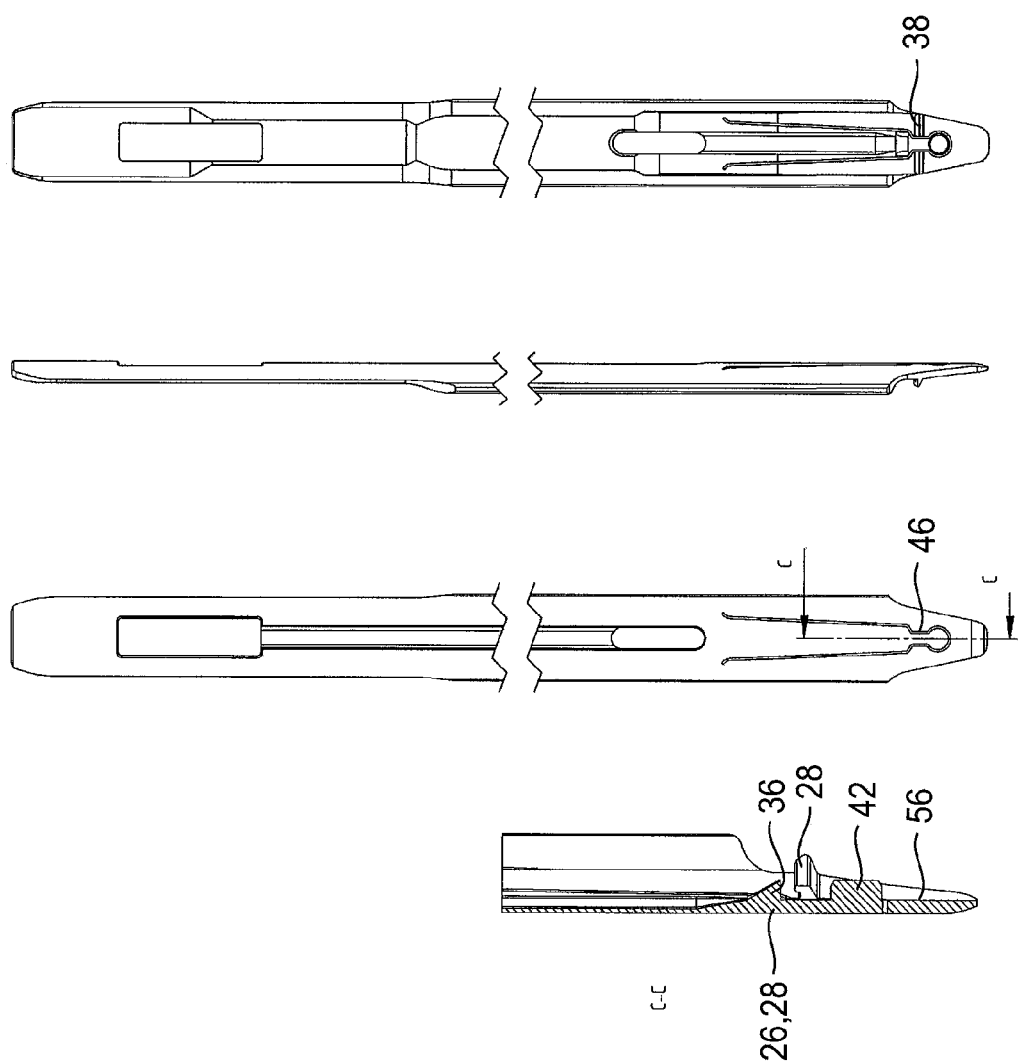

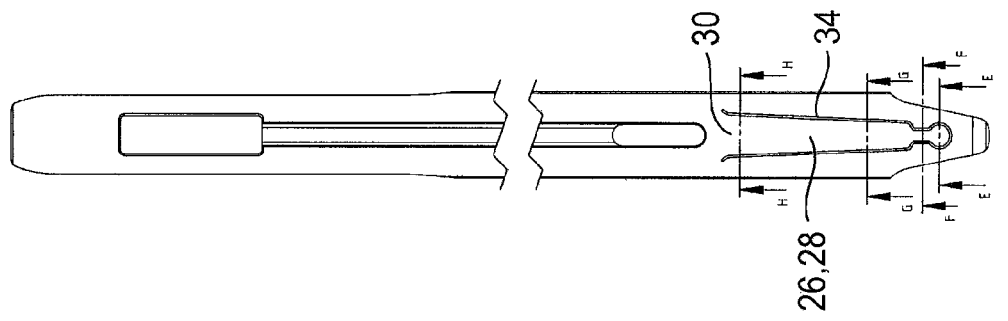

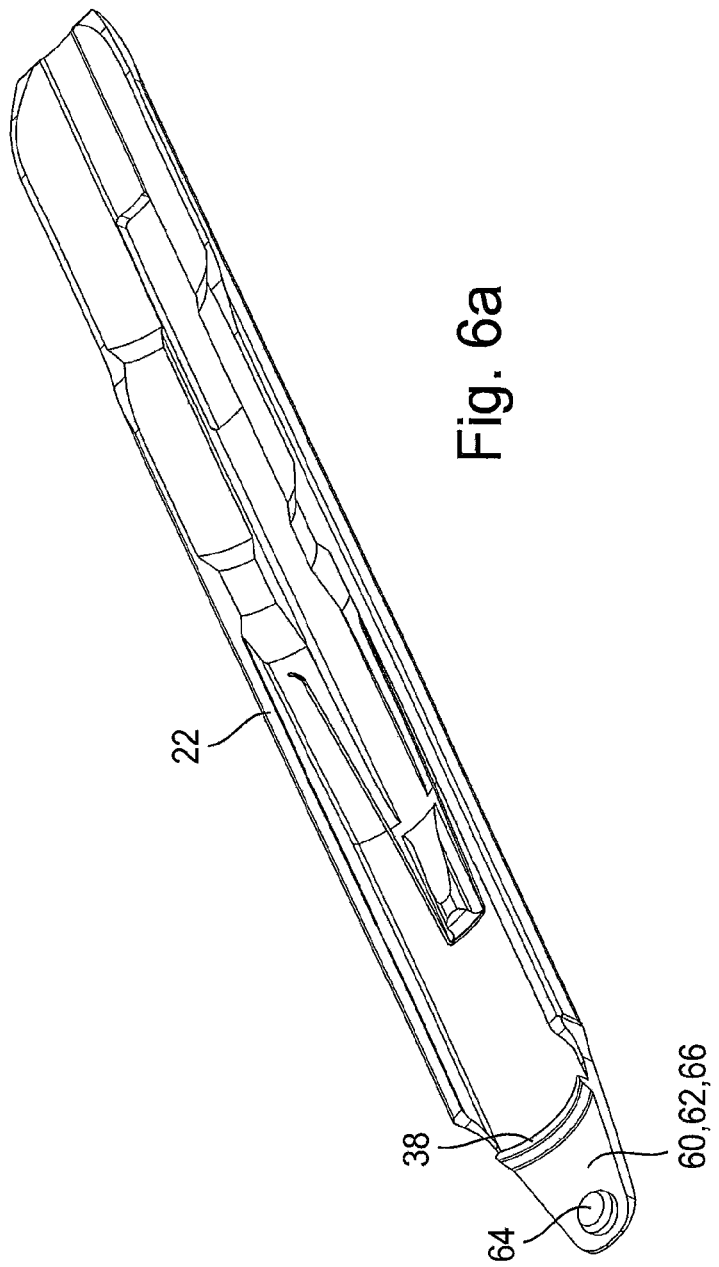

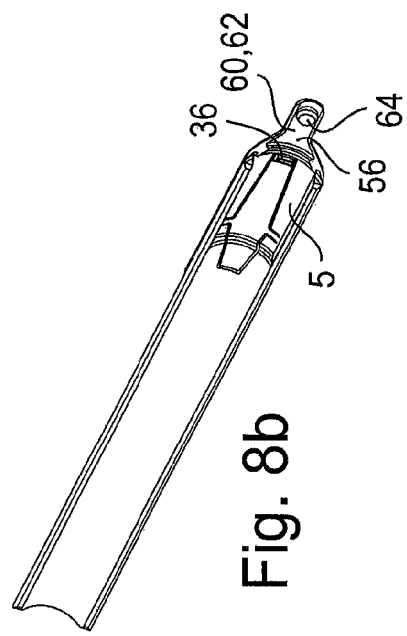
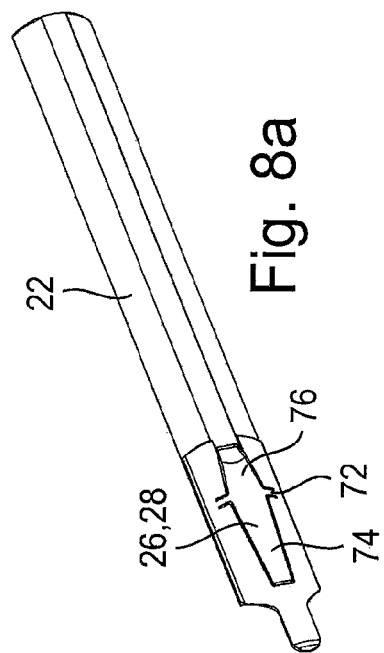

EXTENSION DEVICE FOR A BONE ANCHOR

CROSS-REFERENCES TO RELATED APPLICATIONS

This application is the U.S. National Stage application of PCT/EP2018/065987, filed Jun. 15, 2018, which claims priority to German Patent Application No. 10 2017 114 273.8, filed on Jun. 27, 2017, the disclosure of each of which is incorporated herein by reference in its entirety.

BACKGROUND

The invention relates to an extension device for a bone anchor, in particular for a bone screw, in particular for a pedicle screw, in particular in minimally invasive spinal surgery, having an axial longitudinal direction, a peripheral direction concentric therewith, and a radial direction, the extension device extending in the axial longitudinal direction and engaging, by means of a radial projection, an engageable region on the head of the bone anchor in the longitudinal direction and also in the radial direction and being supportable against the head of the bone anchor in the opposite direction such that the extension device can thereby be fixed to the head of the bone anchor so as to be detachable, yet also rigid in the longitudinal direction and non-rotatable.

Extension devices of the aforementioned type are preferably used in minimally invasive procedures, in particular for the implantation of bone anchors. During the surgical procedure, said devices should somehow keep a working channel to the bone anchor accessible, by means of which channel the surgeon can secure the bone anchor in place by means of further instruments, optionally supply and secure in place further implant parts, and carry out repositioning measures.

An extension device comprising two separate shell parts is known, for example, from WO 2007/021588 A1. These shell parts have to be secured to the head of the bone anchor by means of a further assembly part that connects the two parts. Radial engagement of the shell parts on the head of the bone anchor does not appear to be provided.

SUMMARY OF THE INVENTION

The object of the present invention is to provide an extension device for a bone anchor, which can be easily detachably fastened to the head of the bone anchor before or after the bone anchor is implanted, wherein the extension device should be able to be reliably prevented from becoming unintentionally detached.

According to the invention, this object is achieved in an extension device of the type mentioned by the extension device comprising at least one, preferably two separate shell parts that extend in the longitudinal direction, each of which parts comprises a radial projection for engaging the engageable region on the head of the bone anchor, by the shell part being, for the most part, substantially rigid, but having a first deformable region, by the first deformable region forming a spring element which extends in the axial longitudinal direction and can be deflected transversely to said direction, in particular substantially radially outwardly, by the spring element comprising, proximally to the radial projection for engaging the engageable region on the head of the bone anchor, a radially inwardly projecting support region, by means of which the spring element and thus the shell part is supportable against the head of the bone anchor in the axial longitudinal direction such that the extension device can thereby be detachably fixed to the head of the bone anchor when the projection engages the engageable region on the head of the bone anchor, and by the spring element being deflectable radially outwardly so as to detach the extension device, such that the support region of said spring element is freed from the head of the bone anchor and the shell part can be moved relative to the head of the bone anchor distally out of the engageable region on the head of the bone anchor in the longitudinal direction.

Although two shell parts are preferably used so that these two shell parts can form a working channel, it is conceivable in principle to work with only one shell part in certain situations. If two shell parts are used, it has been found to be advantageous for them both to be designed according to the invention and preferably so as to be identical to one another or so as to correspond to one another.

The extension device according to the invention or the relevant shell part thereof can be fixed to the head of the bone screw, without a force being required to hold it directly thereon. The fixing or holding connection is instead achieved by means of an interlocking connection with respect to all degrees of freedom. As a result of the first deformable region or the spring element formed thereby being deflectable transversely to the longitudinal direction, but comprising a radially inwardly projecting support region, by means of which said region or element is supported, in the holding connection, against the head of the bone anchor in the axial longitudinal direction, the shell part is captively fixed to the head of the bone anchor in the axial direction, since, on account of the axial support, the radial projection of the shell part is prevented from detaching from the engageable region on the head of the bone anchor in the distal direction. At the same time, there can be interlocking holding in the peripheral direction by means of the support region. It is also conceivable, however, for this to be alternatively or additionally achieved in a different way, namely, for example, by a further spring element or by lateral inwardly directed longitudinal edge regions of the shell part, which rest against longitudinal sides of the legs of the head of the bone anchor, or by means of the radial projection of the shell part itself, which engages in the engageable region on the head of the bone anchor, which region is correspondingly provided with peripheral stops.

According to one design variant, so as to join, i.e. establish the releasable holding or fixing connection between, the relevant shell part and the head of the bone anchor, the shell part is positioned on the outer periphery of the bone anchor such that the radial projection of the shell part is distal to the engageable region on the head of the bone anchor. The shell part is then moved relative to the bone anchor in the proximal direction until the radial projection engages in or is latched into the engageable region on the head of the bone anchor and thereby also engages said region in the radial direction. In this position, the spring element can pivot radially inwardly in a resilient manner and thus reach the support region of the spring element supported axially on the head of the bone anchor. The shell part is thus held captively on the head of the bone anchor. In order to release this holding connection, the spring element has to be deflected outwardly, which preferably requires the use of an instrument specially designed for this purpose, in order to reliably prevent unintentional detachment.

According to one embodiment of the invention, it has been found to be advantageous for the spring element to be integral with the shell part and to transition, at its proximal end, into a wall of the shell part. In this way, the spring element and the shell part can be made from the same material; the spring element does not need to be subsequently mounted on said part.

It has also been found to be advantageous for the spring element to be delimited by a material-free slot in the wall of the shell part and to integrally transition, at its proximal end, into the wall of the shell part.

Furthermore, it has been found to be advantageous for the material-free slot to extend in a proximally curved manner, in particular with a radius of curvature of from 0.5 to 5 mm. As a result, when the spring element is being deflected, the tension can be distributed more evenly over a larger area in the wall of the shell part, and early fatigue can be prevented. Alternatively or additionally, it has been found to be advantageous for the material-free slot to lead, at its end, into an opening that is larger than the slot width. This also allows forces introduced by the spring element being deflected to be distributed more evenly.

For the design of the spring element, it may prove to be advantageous for the spring element to have, in a region of its spring arm proximal to the radially inwardly projecting support region, a wall thickness that increases in the axial longitudinal direction in the proximal direction. In particular, in addition to the aforementioned measure, it may prove to be advantageous for the spring element to have in the peripheral direction, in a region of its spring arm proximal to the radially inwardly projecting support region, a width that increases in the axial longitudinal direction in the proximal direction. Furthermore, it may prove to be advantageous for the spring element to be made integral with the shell part by it being freely formed from a previously continuous wall of the shell part by a cut, milling or some other form of material removal. Alternatively, additive manufacturing processes, in particular 3D printing, are conceivable, during which processes the shell part can be produced together with the first deformable region or the spring element. Moreover, a combination of these manufacturing processes is conceivable. Metal alloys and radiolucent materials are conceivable as the raw materials.

In a very particularly preferred embodiment of the invention, it is proposed that the spring element extends in the longitudinal direction distally beyond the radial projection for engaging the engageable region on the head of the bone anchor, and comprises at this point a radially inwardly projecting engagement portion which can be latched into an engagement recess in the head of the bone anchor and can establish an additional interlocking connection between the shell part and the head of the bone anchor. According to this proposal, the spring element not only forms the axial support region, which is provided proximally to the radial projection, but additionally extends further in the distal direction and comprises at this point the aforementioned engagement region, which brings about an additional interlocking engagement between the shell part and the head of the bone anchor. This additional interlocking connection is released again when the spring element is outwardly deflected, as in the case of the axial support.

In a further design of this preferred embodiment, it has been found to be advantageous for the radial projection for engaging the engageable region on the head of the bone anchor to extend in the peripheral direction, and for this radial projection and a wall of the shell part to have gaps or recesses in the peripheral direction in the region of the spring element so that the spring element can then extend therethrough in the axial longitudinal direction. It is in particular advantageous for the spring element to break through the radial projection as a result of extending distally beyond said radial projection so that the spring element does not outwardly protrude radially outside of the shell part, which would also be conceivable in principle.

Furthermore, in this context, it has been found to be advantageous for the spring element to be tapered or necked in the peripheral direction in the region of the radial projection for engaging the engageable region on the head of the bone anchor. In this case, the gap in the radial projection of the shell part is kept smaller in the peripheral direction.

According to a further embodiment of the invention, it is proposed that the shell part comprises, distally to the radial projection for engaging the engageable region on the head of the bone anchor, a second deformable region, which forms a second spring element, the second spring element comprising a second radially inwardly projecting engagement region which can be latched into an engagement recess in the head of the bone anchor and can establish an additional interlocking connection between the shell part and the head of the bone anchor (FIGS. 6, 7 and 8). In this embodiment, the first spring element (unlike in the embodiment explained above) can be clearly proximal to the radial projection and, in particular by comparison with the above-described embodiment, can also be arranged at a distance from the projection in the proximal direction (cf. FIGS. 6 and 7). The second deformable region and the second spring element formed thereby can in this case be designed so as to be detached from the first spring element distally to the radial projection of the shell part.

In a development of this embodiment, it may prove advantageous for the second deformable region of the shell part to be formed by a tapered distal end portion of the shell part. Alternatively or additionally, it may prove to be advantageous for the second deformable region, in particular the distal end portion of the shell part, to comprise weakened portions, in particular in the form of grooves or slots, or to have a lower wall thickness than substantially rigid regions of the shell part.

According to a further embodiment of this variant of the invention, it may prove to be advantageous for the second spring element to be U-shaped and to have two legs and a transverse connecting piece which connects them together, for the engagement region to be formed on the transverse connecting piece, and for the spring element to be integrally attached to the shell part by ends of the legs (FIG. 7).

In this case, it may prove advantageous for the two legs to extend substantially in the longitudinal direction and to continue the extension of the shell part in the longitudinal direction.

According to a further embodiment of the extension device according to the invention (FIG. 8), the first deformable region and the spring element formed thereby are designed in the manner of a rocker and have a rocker arm which is distal to a pivot pin and a rocker arm which is proximal to the pivot pin.

In this embodiment, it may prove advantageous for it to be possible for the spring element to be brought into a release position by the proximal rocker arm being deflected radially inwardly so that the distal rocker arm is thereby deflected radially outwardly and is freed from the head of the bone anchor.

In the embodiments of the invention described above, the first and optionally the second deformable region, and the relevant spring element, are preferably designed and arranged such that the spring element is latched by the spring tension to the head of the bone anchor in its relevant holding connection. This can be facilitated by instruments. In order to release the holding connection, a deflection movement has to therefore be performed on the relevant spring element. This occurs advantageously and preferably at least in the case of the first spring element by a release instrument being brought onto the spring element. For this purpose, it has been found to be advantageous for the shell part to have a channel-forming access opening which extends in the longitudinal direction, through which opening access to the spring element can be gained by means of the release instrument and the spring element can be deflected (radially outwardly) so as to detach the extension device.

It has also been found to be advantageous for the spring element to have an inclined run-on surface for a release instrument. It may prove to be advantageous for the inclined run-on surface to be formed by a proximal side of the support region of the spring element.

If the first spring element is designed in the manner of a rocker, it has been found to be advantageous for the inclined run-on surface to be formed by an outer side of the proximal rocker arm.

The channel-forming access opening may be formed in a wall of the relevant shell part, but it may also be delimited by said wall only in portions. It may be outwardly open in the radial direction in portions, in particular groove-like. Furthermore, the channel-forming access opening may be radially outwardly open in some portions and radially inwardly open in some portions along its extension in the longitudinal direction. Moreover, the channel-forming access opening can communicate with a radial through-opening in the shell part.

For all embodiments according to the invention described above, the following design features have been found to be advantageous:

It has been found to be advantageous for the shell part to have at least one, preferably two inwardly directed longitudinal edge regions, by means of which said part can be positioned against a leg of a head of the bone anchor that is U-shaped in a side view by sides that are opposite in the peripheral direction, such that the shell part can be thereby arranged on the head of the bone anchor such that it cannot rotate in the peripheral direction.

These inwardly directed longitudinal edge regions can then also be used as longitudinal guide means when joining the shell part to the head of the bone anchor.

Furthermore, it has been found to be advantageous for the shell part to have a first support contact surface and a second support contact surface, and for the first support contact surface to be provided distally to the radial projection for engaging the engageable region on the head of the bone anchor and for the second support contact surface to be provided proximally to the radial projection for engaging the engageable region on the head of the bone anchor such that the shell part can be extensively positioned and supported against an outer side of the head of the bone anchor distally and proximally to the projection. In this way, the shell part in question can be particularly advantageously stabilized against the outer side of the head of the bone anchor. Since the outer side of the head of the bone anchor and, accordingly, the first and second support contact surface of the shell part are curved, in particular in the manner of an arc or cylinder, the shell part can be completely prevented from tilting relative to the head of the bone anchor. The shell part is then stabilized with respect to all six degrees of freedom and immovably held on the head of the bone anchor, at least for as long as the actuating forces exerted by the pivot lever element are not deliberately and intentionally counteracted in order to release the shell part again.

Furthermore, it has been found to be advantageous for the radial projection of the relevant shell part to extend in the peripheral direction and to have an inclination, bevel or extension in the proximal direction such that it can form an engagement in the longitudinal direction and radial direction with an engageable region on the head of the bone anchor, which region is approximately complementary to said projection and extends in the peripheral direction. In particular, it has been found to be advantageous for the projection to have a peripheral length which corresponds to the peripheral length of the engageable, typically groove-type region on the head of the bone screw.

The invention also relates to an assembly consisting of an extension device according to one or more of the preceding claims and a bone anchor, in particular a pedicle screw for spinal surgery. It has been found to be advantageous for the bone anchor, in particular the pedicle screw, to have two legs that extend in the longitudinal direction and comprise an internal thread and a predetermined breaking point, in order for it to be possible to break, and thereby shorten, the legs at the predetermined breaking point after implantation. If such a bone anchor having a "long head" is used, its extended internal threaded region can be used to screw in and fix other handling devices and instruments during implantation.

Further features, details and advantages of the extension device according to the invention can be found in the enclosed claims, in the drawings and in the following description of embodiments of the invention.

BRIEF DESCRIPTION OF THE DRAWINGS

In the drawings:

FIG. 1a is a perspective view of a bone anchor in the form of a pedicle screw and an extension device according to the invention comprising two shell parts;

FIG. 1b shows the components of the bone anchor from FIG. 1a in a releasable holding connection;

FIG. 2a-f are various views of the bone anchor from FIG. 1b;

FIG. 3a-f are various views of the shell part of the bone anchor from FIGS. 1a and b;

FIG. 4a-e are a plan view and various sectional views of the shell part of the bone anchor from FIGS. 1a and b;

FIG. 6a-c are various views of a shell part according to a further embodiment of the extension device according to the invention;

FIGS. 8a and b are two perspective views of a shell part according to a further embodiment of the extension device according to the invention;

DETAILED DESCRIPTION

Figure 2A:
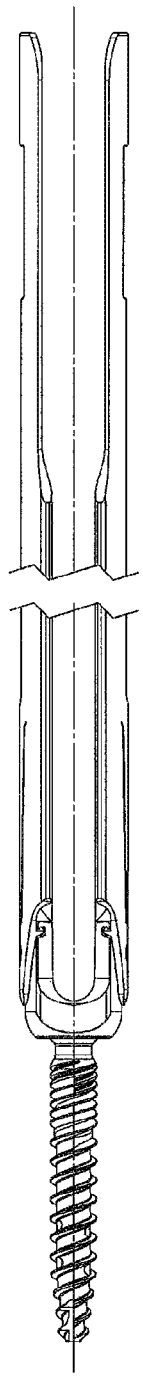
Figure 2B:
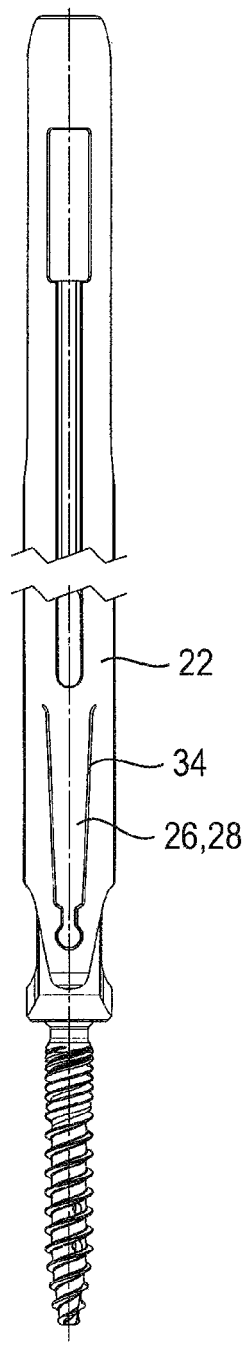

FIGS. 1 to 4 show a first embodiment according to the invention of the extension device 2 according to the invention, partly in a releasable holding connection to a bone anchor 4 in the form of a pedicle screw shown by way of example. The bone anchor 4 comprises a screw shaft 6, which is arranged so as to be polyaxially pivotable relative to a head 8 of the pedicle screw 4, which is U-shaped when viewed from the side. By way of example, the head 8 is what is referred to as a "long head," which is designed having longer legs 10, a predetermined breaking point 12 being provided, at which the long shaft can be shortened when implanted. Nevertheless, the head 8 of the bone anchor 4 comprises, in a manner known per se, an engageable region 14, which is in the form of an engageable groove in the outer periphery of the head 8. Incidentally, the engageable region 14 of the head 8 can be designed according to the disclosure in the applicant's patent application DE 10 2014 225 327.6, the content of which is to be incorporated in the disclosure of the present application.

The extension device 2 has an axial longitudinal direction 16, a peripheral direction 18 concentric therewith and a radial direction 20, which all relate to the head 8 of the bone anchor 4. The extension device 2 comprises two separate shell parts 22 that extend in the longitudinal direction 16 and have, by way of example and preferably, a corresponding design. The shell parts 22 are substantially rigid and resistant to torsion in the sense that they are almost completely dimensionally stable, but slight, insignificant deformability, in particular due to the length, is not ruled out. The shell parts 22 can be detachably secured to the head 8 of the bone anchor 4 in a manner to be described below, and then form a working channel 24 which is delimited between said parts and through which the surgeon can gain access to the bone anchor 4 and the surgical environment using other instruments.

A particular shell part 22 is substantially dimensionally stable, but comprises a first deformable region 26, which at the same time forms a first spring element 28, which extends in the axial longitudinal direction 16 and can be deflected transversely thereto approximately radially outwardly. In the embodiment shown, by way of example, the spring element 28 is integral with the shell part 22 and integrally transitions, at its proximal end 30, into a wall 32 of the shell part 22. The first deformable region 26 or the spring element 28 is delimited by a material-free slot 34 in the wall 32 of the shell part 22. The material-free slot 34 extends, at its proximal ends, in a curved manner, which causes tension to be introduced into the shell part 22 in an even manner. It can be seen from the plan view of FIG. 4a that the spring element 28 has an increasing width in the proximal direction and an increasing thickness in the peripheral direction (FIGS. 4b and 4c). The spring element 28 also comprises a radially inwardly projecting support region 36, by means of which the spring element 28 and thus the shell part 22 can be supported against the head 8 of the bone anchor 4 in the axial longitudinal direction 16. This support region 36 is arranged proximally to a radial projection 38 of the shell part 22 in the longitudinal direction 16. The radial projection 38 is formed in the peripheral direction 18 in the form of an inwardly projecting rib, which also has an extension in the proximal direction so as to be able to engage in the engageable region 14 on the head of the bone anchor. FIG. 3b best shows the extension of the radial projection 38 in the peripheral direction 18. In the embodiment according to FIGS. 1 to 4, the radial projection 38 has a central gap 40 so that the spring element 28 can extend distally through the radial projection 38 in the longitudinal direction 16. In the region distal to the radial projection 38, the spring element 28 comprises a radially inwardly projecting engagement region 42 which can engage in an engagement recess 44 in the head 8 of the bone anchor 4 and can establish an additional interlocking connection between the shell part 22 and the bone anchor 4. The spring element 28 is also designed such that it comprises, in the region of the central gap 40 in the radial projection 38, a tapered or necked portion 46, i.e. it is designed such that it is narrower at this point in the peripheral direction.

As described at the outset, the shell part 22 in question is held on the head 8 of the bone anchor 4 so as to be detachable, but interlockingly connected thereto with respect to all degrees of freedom, as can be best seen in FIGS. 2e and f, by it being hooked behind the engageable region 14 of the head 8 of the bone anchor in the longitudinal direction 16 and radial direction 20 by its radial projection 38 and being supported axially against the head 8 by its support region 36 in the opposite direction. In the above-described embodiment, the spring element 28 further engages, by its distal engagement region 42, in the engagement recess 44 in the head 8. It can be seen from FIG. 2f that the relevant shell part 22 has two inwardly directed longitudinal edge regions 54, by means of which it rests against the leg 10 of the head 4 of the bone anchor by lateral support surfaces 55 of sides that are opposite in the peripheral direction 18. The shell part 22 thus surrounds the leg 10 substantially with at least almost zero clearance and is thus also non-rotatably held in the peripheral direction 18, in addition to the engaging elements.

Overall, an operating connection is established here that is an interlocking connection with respect to all degrees of freedom, which connection can be released by the spring element 28 being outwardly deflected in the radial direction 20. This can be achieved by access being gained to the spring element 28 by means of a release instrument (not shown). For this purpose, in the relevant shell part 22, a channel-forming access opening 50 that extends in the longitudinal direction 16 is formed, which is radially outwardly open in some portions and radially inwardly open in some portions along its extension in the longitudinal direction 16, and is delimited by the spring element 28 itself. The channel-forming access opening also passes through a radial through-opening 51 in the shell part 22 that extends in the longitudinal direction 16. In the case shown by way of example, the spring element has an inclined run-on surface 52 for the release instrument, specifically on its inner side and on a proximal side of its support region 36.

Figure 5:
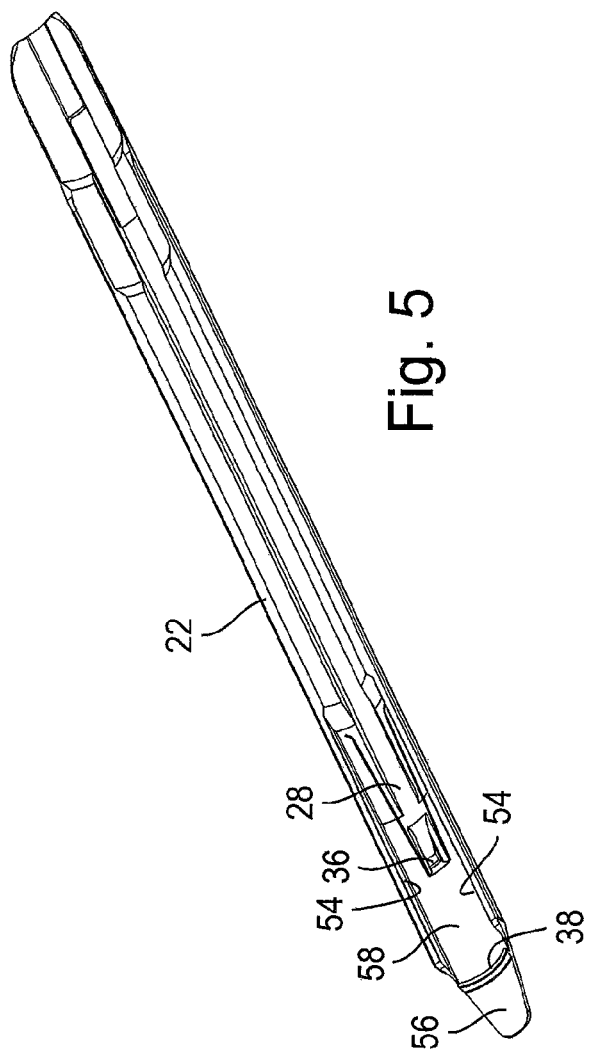
FIG. 5 is a perspective view of a shell part according to a further embodiment of the extension device according to the invention.

FIG. 5 shows a reduced embodiment by comparison with the previously described embodiment, in which the spring element 28 does not extend beyond the radial projection 38 in the distal direction. Furthermore, it can be seen preferably and by way of example that a particular shell part 22 has a first support contact surface 56 and a second support contact surface 58, which are formed distally and proximally to the radial projection 36, respectively. They are designed according to the curvature of the outer side of the head 8 such that the shell part 22 can be extensively positioned and supported against the outer side of the head of the bone anchor distally and proximally to the projection 36. In cooperation with the interlocking engagement, this also causes additional stabilization of the holding connection.

The shell part 22 according to FIG. 5 can therefore be fixed against the head of the bone anchor by the engagement of its radial projection 38 in the engageable region 14 on the head of the bone anchor and by the axial support by means of the support region 36. In this case, the lateral longitudinal edge regions 54 form an interlocking connection to the relevant leg 10 of the head of the bone anchor, and the support contact surfaces 56, 58 additionally stabilize the holding connection.

Figure 6B:
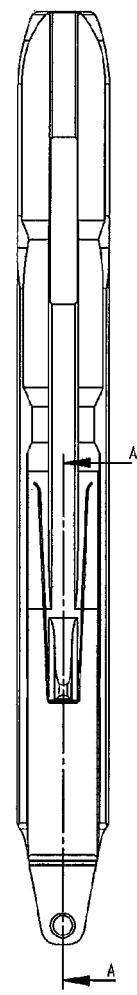
Figure 6C:
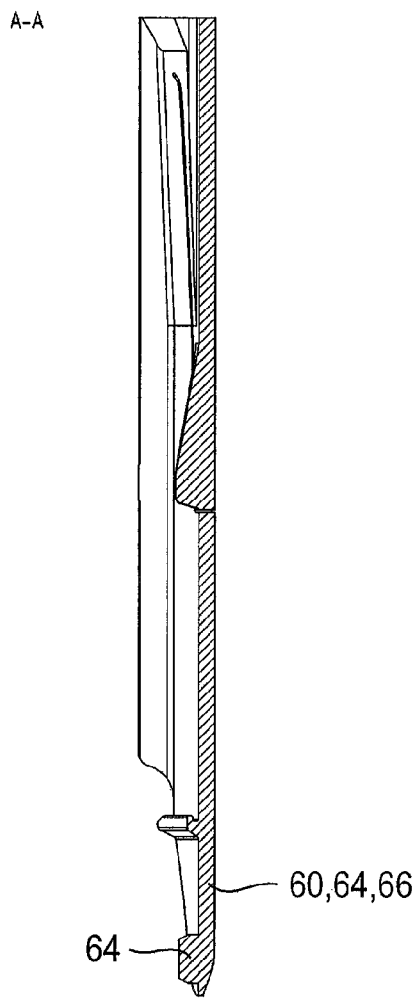
Figure 7A:
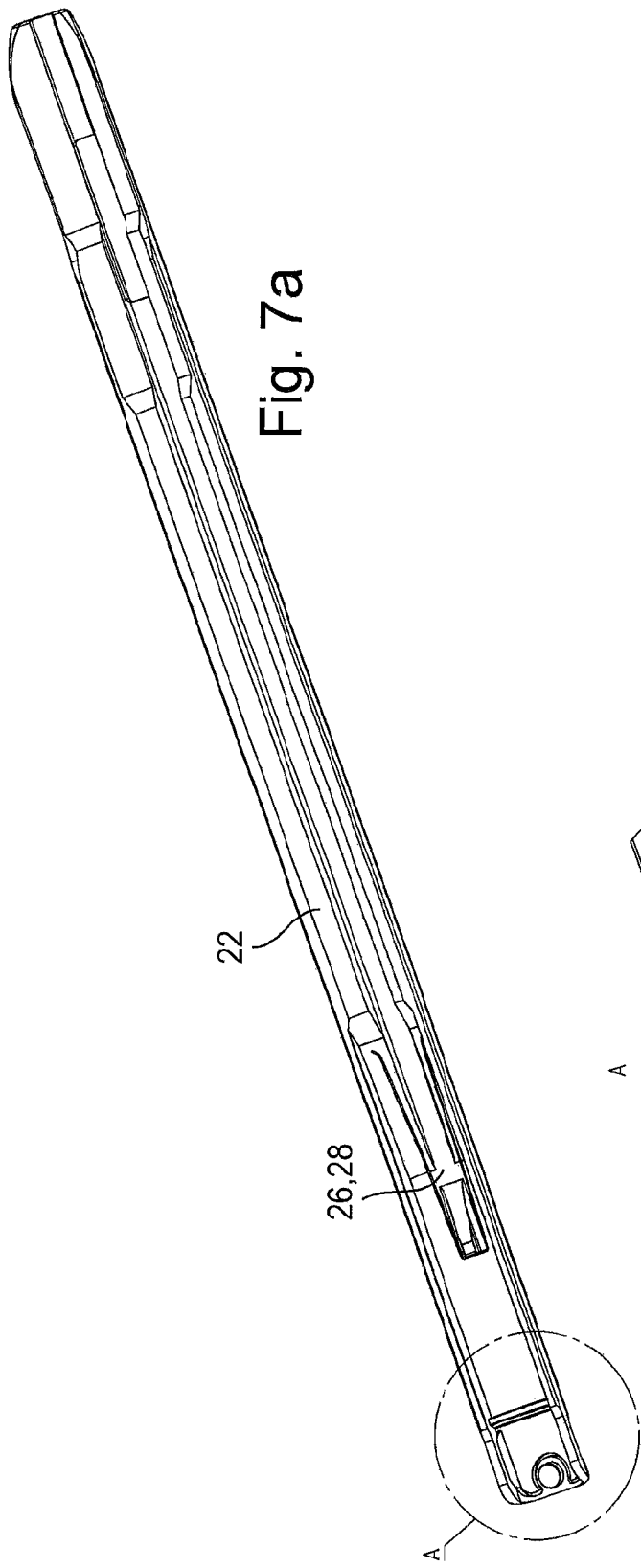
FIG. 7a-e are various views of a shell part according to a further embodiment of the extension device according to the invention.
Figure 7B:
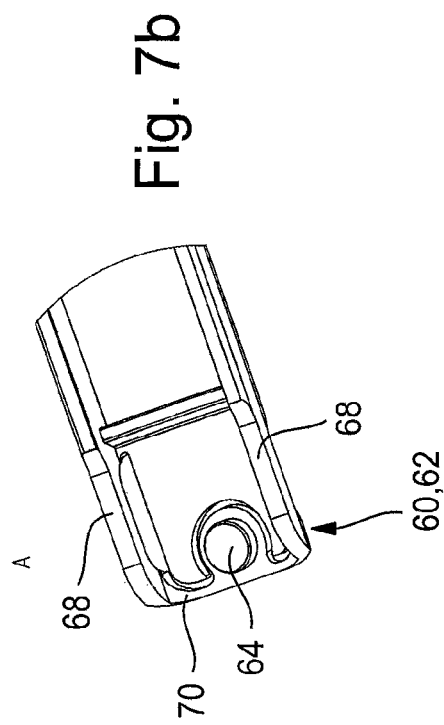
Figure 7C:
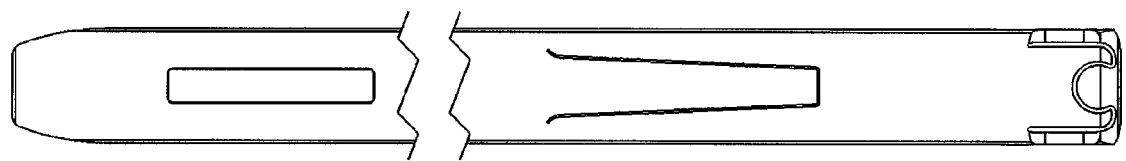
Figure 7D:
Figure 7E:
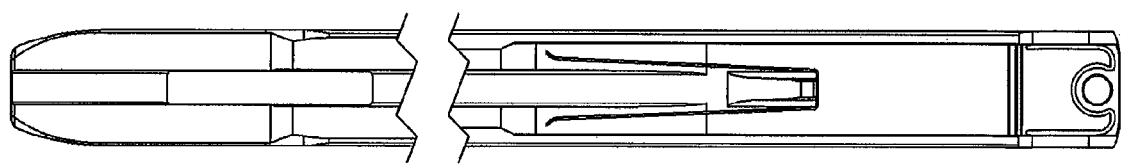

The further embodiment according to FIG. 6a to c uses the embodiment according to FIG. 5 as a starting point. The shell part 22 shown here additionally has a second deformable region 60, which forms a second spring element 62 having a radially inwardly projecting engagement region 64. The second deformable region 60 is, in the present case, distal to the radial projection 38 and formed by a tapered distal end portion 66 of the shell part 22, which is resilient transversely to the longitudinal direction. This can be achieved by weakened portions in the form of grooves or slots (not shown) or a lower wall thickness than in adjoining substantially rigid regions of the shell part 22.

In the embodiment according to FIG. 7a to e shown by way of example, in addition to the first deformable region 26 comprising a first spring element 28, a second deformable region 60 comprising a second spring element 62 is likewise provided. The second spring element 62 is U-shaped in this case and comprises two legs 68 which extend in the longitudinal direction 16, and a connecting piece 70 which connects them together. An engagement region 64 is in turn formed on this connecting piece 70. The spring element 62 is integrally attached to the shell part 22 by its legs 68.

In the embodiment according to FIG. 8a, the first deformable region 26 or the first spring element 28 is designed in the manner of a rocker and has a rocker arm 74 which is distal to a pivot pin 72 and a rocker arm 76 which is proximal to the pivot pin. The radially inwardly projecting support region 36 is formed on the proximal rocker arm 76. In this embodiment too, by way of example, a second deformable region 60 is provided, which forms a second spring element 62 comprising an engagement region 64. Furthermore, support contact surfaces 56, 58 that correspond to the curvature of the outer side of the head of the bone anchor are provided.

The invention claimed is:

1. Extension device for a bone anchor comprising an axial longitudinal direction, a peripheral direction concentric therewith, and a radial direction, the extension device extending in the axial longitudinal direction and engaging, by means of a radial projection, an engageable region on a head of the bone anchor in the axial longitudinal direction and also in the radial direction and being supportable against the head of the bone anchor in a direction opposite to the axial longitudinal direction such that the extension device can thereby be fixed to the head of the bone anchor so as to be detachable, yet also rigid in the axial longitudinal direction and non-rotatable, wherein the extension device comprises at least one separate shell par that extends in the axial longitudinal direction, the at least one shell part comprises the radial projection for engaging the engageable region on the head of the bone anchor, in that the shell part is rigid, but has a first deformable region, in that the first deformable region forms a spring element which extends in the axial longitudinal direction and can be deflected transversely to the axial longitudinal direction, in that the spring element comprises, proximally to the radial projection for engaging the engageable region on the head of the bone anchor, a radially inwardly projecting support region, by means of which the spring element and the shell part is supportable against the head of the bone anchor in the axial longitudinal direction such that the extension device can thereby be detachably fixed to the head of the bone anchor when the radial projection engages the engageable region on the head of the bone anchor, and in that the spring element is deflectable radially outwardly so as to detach the extension device, wherein the support region of said spring element is freed from the head of the bone anchor and the shell part can be moved relative to the head of the bone anchor distally out of the engageable region on the head of the bone anchor in the axial longitudinal direction, wherein the spring element is integral with the shell part, is delimited by a material-free slot in a wall of the shell part and transitions, at its proximal end, into the wall of the shell part.

2. Extension device according to claim 1, characterized in that the material-free slot extends in a proximally curved manner with a radius of curvature of from 0.5 to 5 mm.

3. Extension device according to claim 1, characterized in that the material-free slot leads, at its end, into an opening that is larger than a width of the slot.

4. Extension device according to claim 1, characterized in that the spring element has, in a region of a spring arm proximal to the radially inwardly projecting support region, a wall thickness that increases in the axial longitudinal direction in the proximal direction.

5. Extension device according to claim 1, characterized in that the spring element has in a region of a spring arm proximal to the radially inwardly projecting support region, a width in the peripheral direction that increases in the axial longitudinal direction in the proximal direction.

6. Extension device according to claim 1, characterized in that the spring element is made integral with the shell part by it being freely formed from a previously continuous wall of the shell part by a cut, milling or some other form of material removal, or by the entire shell part being produced in an additive manufacturing process having an already delimited spring element.

7. Extension device according to claim 1, characterized in that the spring element extends in the axial longitudinal direction distally beyond the radial projection for engaging the engageable region on the head of the bone anchor, and comprises at this point a radially inwardly projecting engagement portion which can be latched into an engagement recess in the head of the bone anchor and can establish an additional interlocking connection between the shell part and the head of the bone anchor.

8. Extension device according to claim 7, characterized in that the radial projection for engaging the engageable region on the head of the bone anchor extends in the peripheral direction, and in that this radial projection and a wall of the shell part has gaps or recesses in the peripheral direction in the region of the spring element so that the spring element can then extend therethrough in the axial longitudinal direction.

9. Extension device according to claim 7, characterized in that the spring element is tapered or necked in the peripheral direction in the region of the radial projection for engaging the engageable region on the head of the bone anchor.

10. Extension device for a bone anchor comprising an axial longitudinal direction, a peripheral direction concentric therewith, and a radial direction, the extension device extending in the axial longitudinal direction and engaging, by means of a radial projection, an engageable region on a head of the bone anchor in the axial longitudinal direction and also in the radial direction and being supportable against the head of the bone anchor in a direction opposite to the axial longitudinal direction such that the extension device can thereby be fixed to the head of the bone anchor so as to be detachable, yet also rigid in the axial longitudinal direction and non-rotatable, wherein the extension device comprises at least one separate shell part that extends in the axial longitudinal direction, the at least one shell part comprises the radial projection for engaging the engageable region on the head of the bone anchor, in that the shell part is substantially rigid, but has a first deformable region, in that the first deformable region forms a spring element which extends in the axial longitudinal direction and can be deflected transversely to the axial longitudinal direction, in that the spring element comprises, proximally to the radial projection for engaging the engageable region on the head of the bone anchor, a radially inwardly projecting support region, by means of which the spring element and the shell part is supportable against the head of the bone anchor in the axial longitudinal direction such that the extension device can thereby be detachably fixed to the head of the bone anchor when the radial projection engages the engageable region on the head of the bone anchor, and in that the spring element is deflectable radially outwardly so as to detach the extension device, wherein the support region of said spring element is freed from the head of the bone anchor and the shell part can be moved relative to the head of the bone anchor distally out of the engageable region on the head of the bone anchor in the axial longitudinal direction, characterized in that the shell part comprises, distally to the radial projection for engaging the engageable region on the head of the bone anchor, a second deformable region, which forms a second spring element, the second spring element comprising a radially inwardly projecting engagement region which can be latched into an engagement recess in the head of the bone anchor and can establish an additional interlocking connection between the shell part and the head of the bone anchor.

11. Extension device according to claim 10, characterized in that the second deformable region of the shell part is formed by a tapered distal end portion of the shell part.

12. Extension device according to claim 10, characterized in that the second deformable region, in a distal end portion, of the shell part, comprises weakened portions or has a lower wall thickness than substantially rigid regions of the shell part.

13. Extension device according to claim 10, characterized in that the second spring element is U-shaped and has two legs and a transverse connecting piece which connects them together, and in that the engagement region is formed on the transverse connecting piece, and in that the second spring element is integrally attached to the shell part by ends of the legs.

14. Extension device according to claim 13, characterized in that the two legs extend substantially in the axial longitudinal direction and continue the extension of the shell part in the axial longitudinal direction.

15. Extension device according to claim 1, characterized in that the shell part has a channel-forming access opening which extends in the axial longitudinal direction, through which opening access to the spring element can be gained by means of a release instrument and the spring element can be deflected so as to detach the extension device.

16. Extension device according to claim 15, characterized in that the spring element has an inclined run-on surface for a release instrument.

17. Extension device according to claim 16, characterized in that the inclined run-on surface is formed by a proximal side of the support region of the spring element.

18. Extension device according to claim 15, characterized in that the channel-forming access opening is outwardly open in the radial direction.

19. Extension device according to claim 15, characterized in that the channel-forming access opening is radially outwardly open in some portions and radially inwardly open in some portions along its extension in the longitudinal direction.

20. Extension device according to claim 15, characterized in that the channel-forming access opening communicates with a radial through-opening in the shell part.

21. Extension device according to claim 1, characterized in that the shell part has at least one inwardly directed longitudinal edge region, by means of which said part can be positioned against a leg of the head of the bone anchor that is U-shaped in a side view by sides that are opposite in the peripheral direction, such that the shell part can be thereby arranged on the head of the bone anchor such that it cannot rotate in the peripheral direction.

22. Extension device according to claim 1, characterized in that the shell part has a first support contact surface and a second support contact surface, and in that the first support contact surface is provided distally to the radial projection for engaging the engageable region on the head of the bone anchor and the second support contact surface is provided proximally to the radial projection for engaging the engageable region on the head of the bone anchor such that the shell part can be extensively positioned and supported against an outer side of the head of the bone anchor distally and proximally to the radial projection.

23. Extension device according to claim 1, characterized in that the radial projection of the shell part extends in the peripheral direction and has an inclination, bevel or extension in the proximal direction such that it can form an engagement in the axial longitudinal direction and radial direction with the engageable region on the head of the bone anchor, which region is approximately complementary to said radial projection and extends in the peripheral direction.

24. Assembly comprising a bone anchor and an extension device for the bone anchor comprising an axial longitudinal direction, a peripheral direction concentric therewith, and a radial direction, the extension device extending in the axial longitudinal direction and engaging, by means of a radial projection, an engageable region on a head of the bone anchor in the axial longitudinal direction and also in the radial direction and being supportable against the head of the bone anchor in a direction opposite the axial longitudinal direction such that the extension device can thereby be fixed to the head of the bone anchor so as to be detachable, yet also rigid in the axial longitudinal direction and non-rotatable, characterized in that the extension device comprises at least one shell part that extend in the axial longitudinal direction, the at least one shell part comprises the radial projection for engaging the engageable region on the head of the bone anchor, in that the shell part is substantially rigid, but has a first deformable region, in that the first deformable region forms a spring element which extends in the axial longitudinal direction and can be deflected transversely to the axial longitudinal direction, in that the spring element comprises, proximally to the radial projection for engaging the engageable region on the head of the bone anchor, a radially inwardly projecting support region, by means of which the spring element and thus the shell part is supportable against the head of the bone anchor in the axial longitudinal direction such that the extension device can thereby be detachably fixed to the head of the bone anchor when the radial projection engages the engageable region on the head of the bone anchor, and in that the spring element is deflectable radially outwardly so as to detach the extension device, such that the support region of said spring element is freed from the head of the bone anchor and the shell part can be moved relative to the head of the bone anchor distally out of the engageable region on the head of the bone anchor in the axial longitudinal direction, wherein the spring element is integral with the shell part, is delimited by a material-free slot in the wall of the shell part and transitions, at its proximal end, into a wall of the shell part.

25. Assembly according to claim 24, characterized in that the bone anchor has two legs that extend in the axial longitudinal direction and comprise an internal thread and a predetermined breaking point, in order for it to be possible to break, and thereby shorten, the legs at the predetermined breaking point after implantation.

26. Extension device for a bone anchor comprising an axial longitudinal direction, a peripheral direction concentric therewith, and a radial direction, the extension device extending in the axial longitudinal direction and engaging, by means of a radial projection, an engageable region on a head of the bone anchor in the axial longitudinal direction and also in the radial direction and being supportable against the head of the bone anchor in a direction opposite to the axial longitudinal direction such that the extension device can thereby be fixed to the head of the bone anchor so as to be detachable, yet also rigid in the axial longitudinal direction and non-rotatable, wherein the extension device comprises at least one separate shell part that extends in the longitudinal direction, the at least one shell part comprises the radial projection for engaging the engageable region on the head of the bone anchor, in that the shell part is substantially rigid, but has a first deformable region, in that the first deformable region forms a spring element which extends in the axial longitudinal direction and can be deflected transversely to said axial longitudinal direction, in that the spring element comprises, proximally to the radial projection for engaging the engageable region on the head of the bone anchor, a radially inwardly projecting support region, by means of which the spring element and the shell part is supportable against the head of the bone anchor in the axial longitudinal direction such that the extension device can thereby be detachably fixed to the head of the bone anchor when the radial projection engages the engageable region on the head of the bone anchor, and in that the spring element is deflectable radially outwardly so as to detach the extension device, wherein the support region of said spring element is freed from the head of the bone anchor and the shell part can be moved relative to the head of the bone anchor distally out of the engageable region on the head of the bone anchor in the axial longitudinal direction, wherein the spring element extends in the axial longitudinal direction distally beyond the radial projection for engaging the engageable region on the head of the bone anchor, and comprises at this point a radially inwardly projecting engagement portion which can be latched into an engagement recess in the head of the bone anchor and can establish an additional interlocking connection between the shell part and the head of the bone anchor and the radial projection for engaging the engageable region on the head of the bone anchor extends in the peripheral direction, and in that this radial projection and a wall of the shell part has gaps or recesses in the peripheral direction in the region of the spring element so that the spring element can then extend therethrough in the axial longitudinal direction.

* * * * *